(12) United States Patent
Yabe

(10) Patent No.: US 8,616,747 B2
(45) Date of Patent: Dec. 31, 2013

(54) LIGHT SOURCE APPARATUS

(71) Applicant: Olympus Medical Systems Corp., Tokyo (JP)

(72) Inventor: Yusuke Yabe, Chofu (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/705,642

(22) Filed: Dec. 5, 2012

(65) Prior Publication Data

US 2013/0148345 A1    Jun. 13, 2013

Related U.S. Application Data

(63) Continuation of application No. PCT/JP2012/052723, filed on Feb. 7, 2012.

(30) Foreign Application Priority Data

Feb. 9, 2011    (JP) .................................. 2011-026370

(51) Int. Cl.
*A61B 1/06* (2006.01)
*F21V 9/00* (2006.01)

(52) U.S. Cl.
USPC ........... 362/574; 362/572; 600/160; 600/178; 600/181

(58) Field of Classification Search
USPC ........................... 362/572–575; 600/160–181
See application file for complete search history.

(56) References Cited

U.S. PATENT DOCUMENTS

| 8,506,478 B2 * | 8/2013 | Mizuyoshi ..................... 600/178 |
| 2004/0037454 A1 | 2/2004 | Ozawa et al. |
| 2006/0178565 A1 | 8/2006 | Matsui et al. |
| 2007/0093688 A1 | 4/2007 | Enomoto |
| 2007/0153542 A1 | 7/2007 | Gono et al. |
| 2008/0255426 A1 * | 10/2008 | Iketani ......................... 600/180 |
| 2009/0122135 A1 | 5/2009 | Matsui |
| 2010/0240953 A1 | 9/2010 | Murakami |
| 2011/0234782 A1 * | 9/2011 | Ehrhardt et al. .............. 362/574 |

FOREIGN PATENT DOCUMENTS

| EP | 1 374 755 A1 | 1/2004 |
| EP | 1 787 577 A1 | 5/2007 |
| EP | 2 229 870 A1 | 9/2010 |
| JP | 2002253494 A * | 9/2002 |

(Continued)

OTHER PUBLICATIONS

International Search Report dated Mar. 6, 2012 issued in PCT/JP2012/052723.

*Primary Examiner* — Mariceli Santiago
(74) *Attorney, Agent, or Firm* — Scully, Scott, Murphy & Presser, P.C.

(57) ABSTRACT

A light source apparatus includes: a white LED that emits light including a first wavelength band and a second wavelength band; a violet LED that emits light in a third wavelength band, and a rotating disk including a filter that transmits light in the first wavelength band. The light source apparatus also includes a rotating disk drive section that changes a position of the rotating disk so that if a normal observation mode is selected, the filter is retracted from an optical path of the light emitted from the white LED, if a narrow band observation mode is selected, a filter is continuously inserted in the optical path of the light emitted from the white LED, and if a twin mode is selected, the filter is intermittently inserted in the optical path of the light emitted from the white LED.

8 Claims, 12 Drawing Sheets

(56) References Cited

FOREIGN PATENT DOCUMENTS

| JP | 2004-024611 | | 1/2004 |
| JP | 2004008412 A | * | 1/2004 |
| JP | 2006-075239 | | 3/2006 |
| JP | 2006-212335 | | 8/2006 |
| JP | 2006-218283 | | 8/2006 |
| JP | 2007-117287 | | 5/2007 |
| JP | 2008-259722 | | 10/2008 |
| JP | 2009-118898 | | 6/2009 |
| JP | 2010-213993 | | 9/2010 |

* cited by examiner

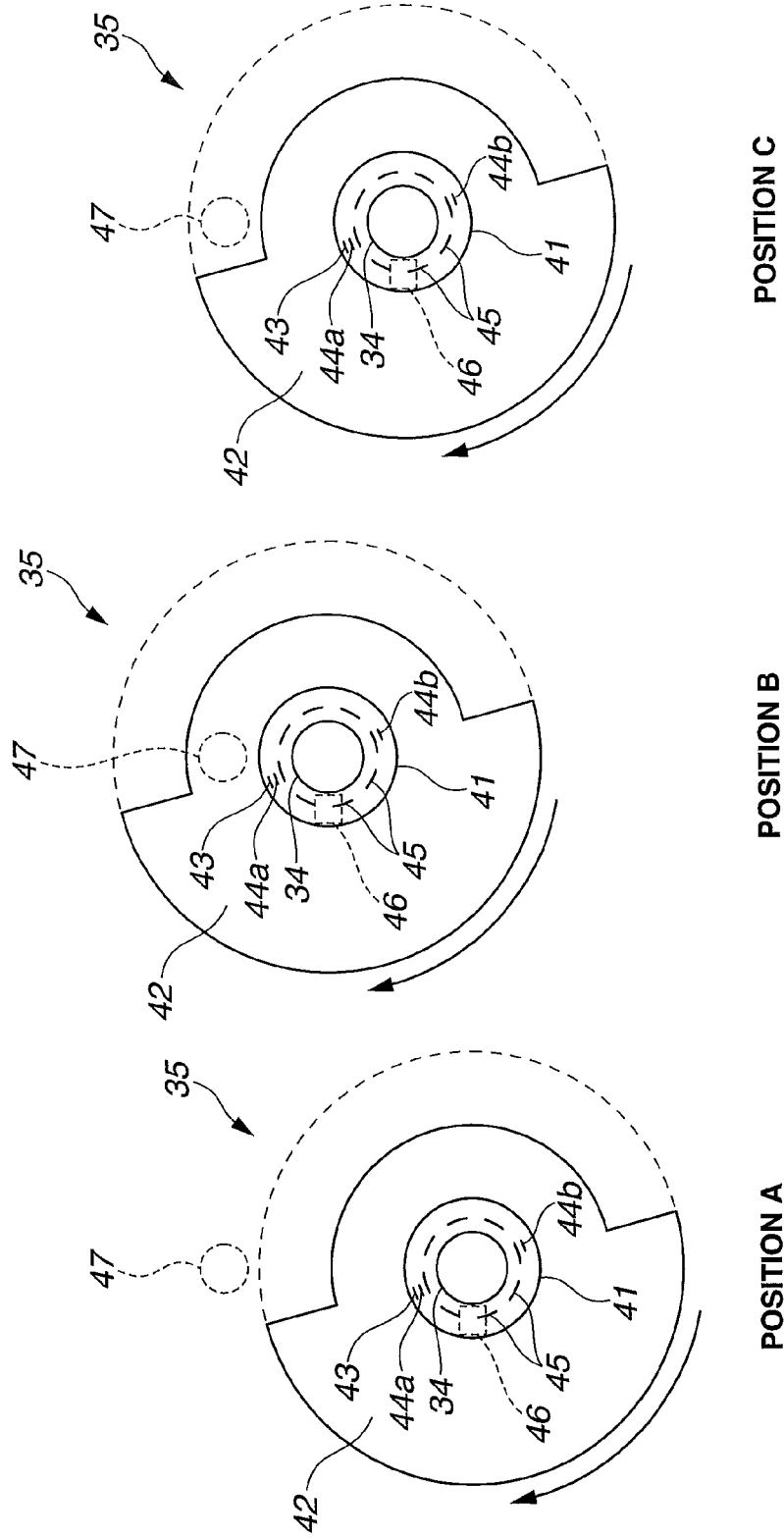

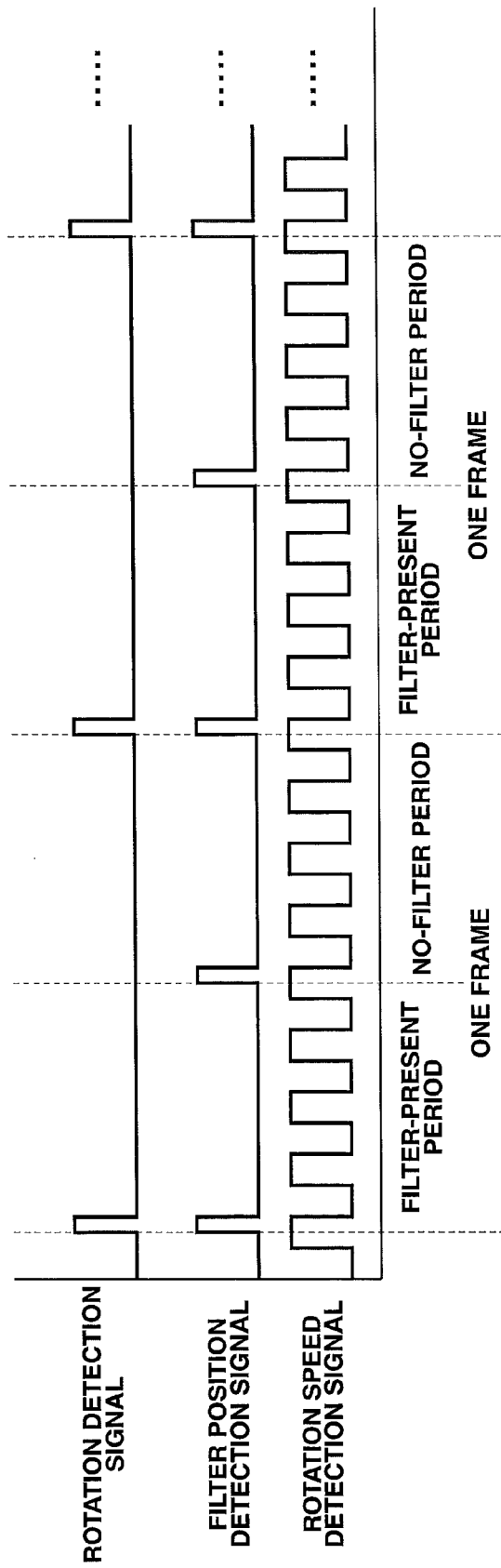

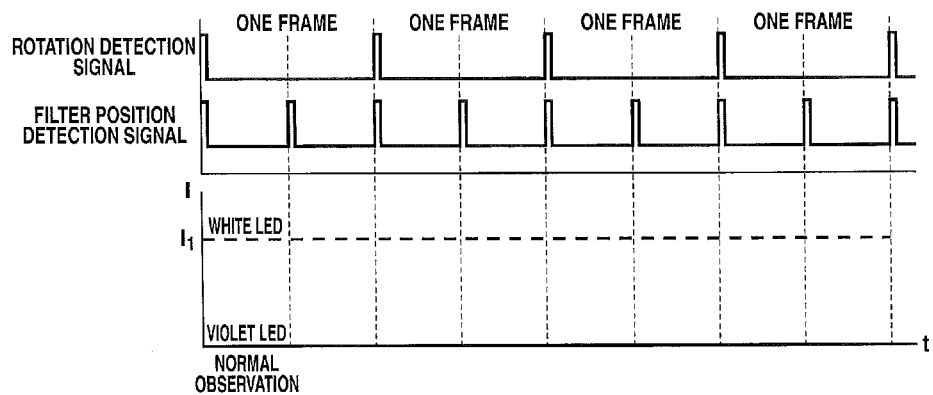
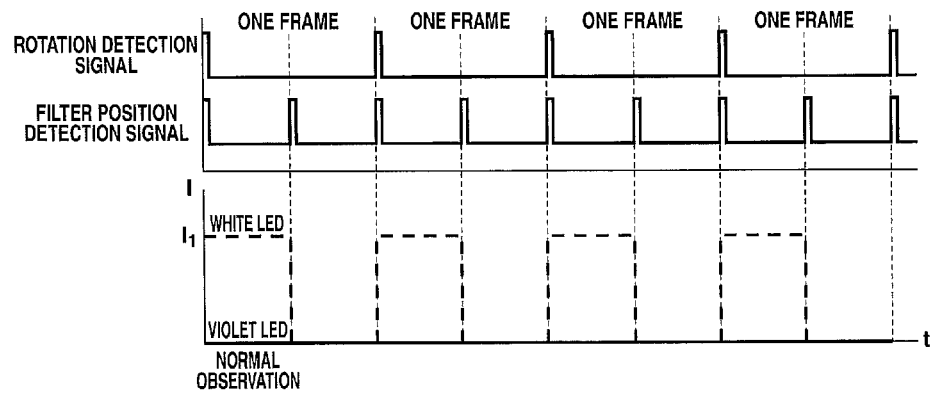
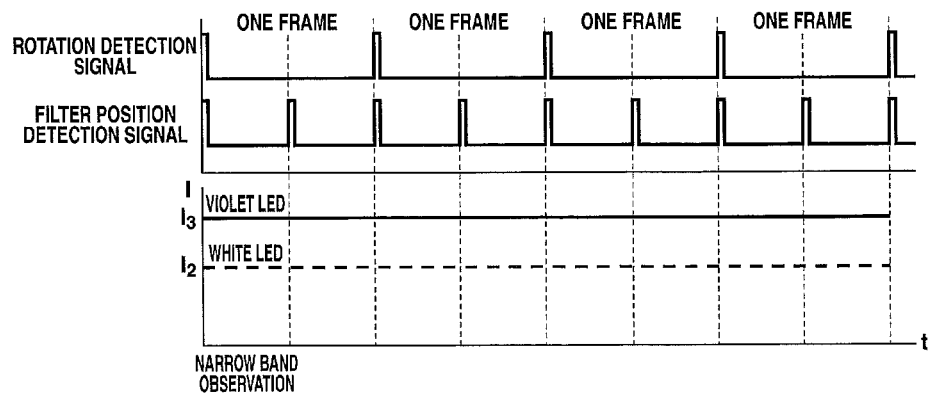

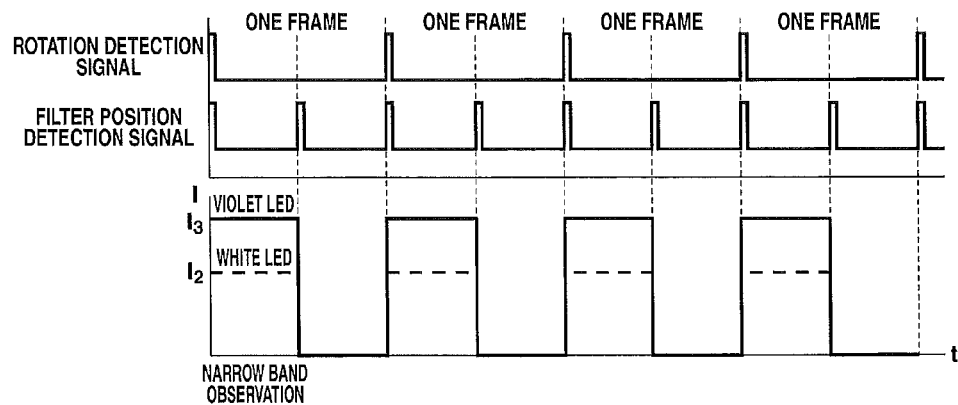
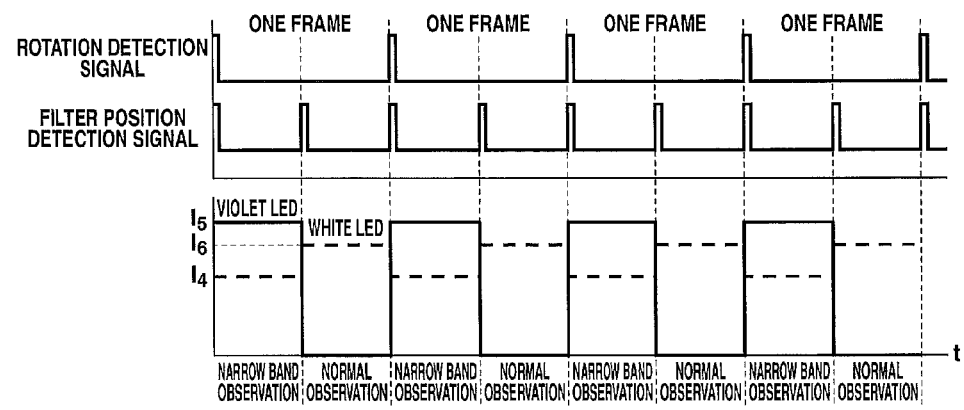
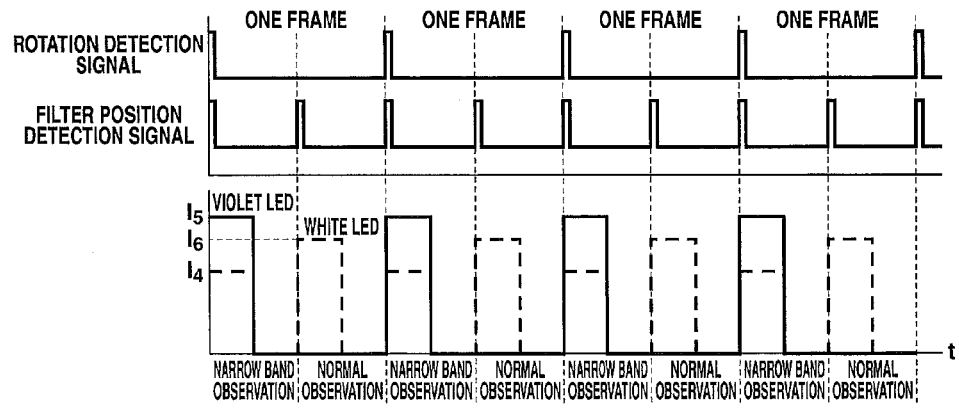

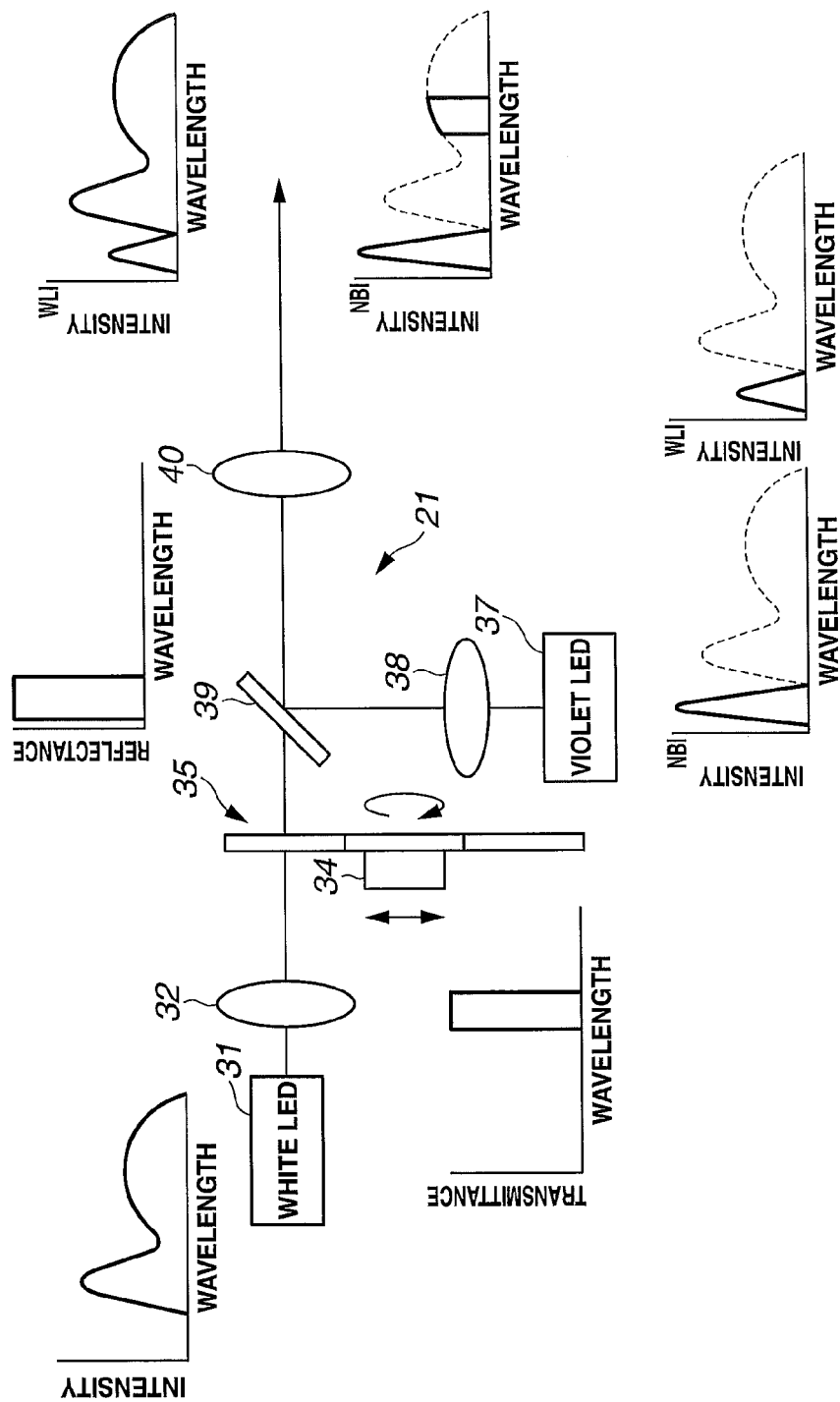

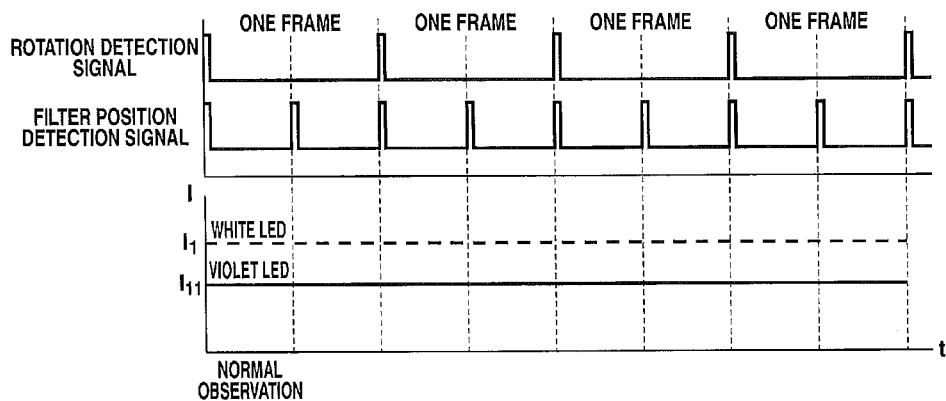
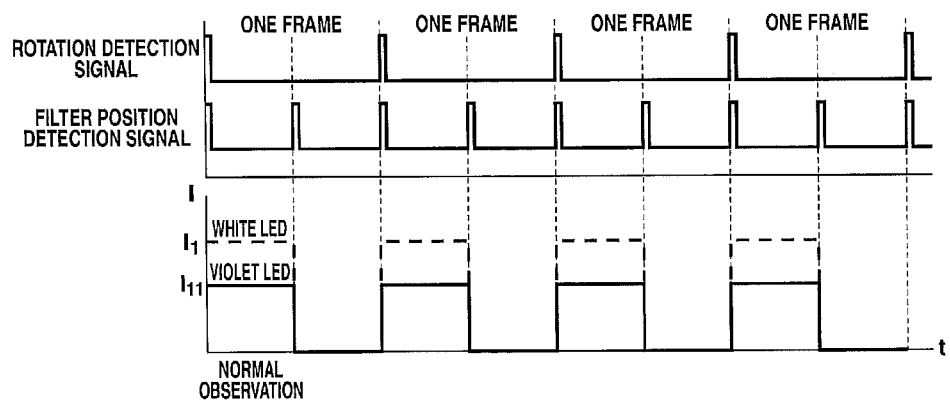
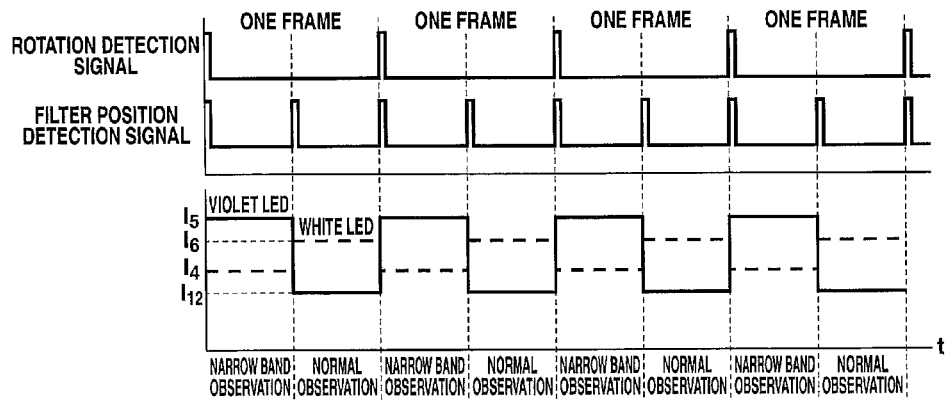

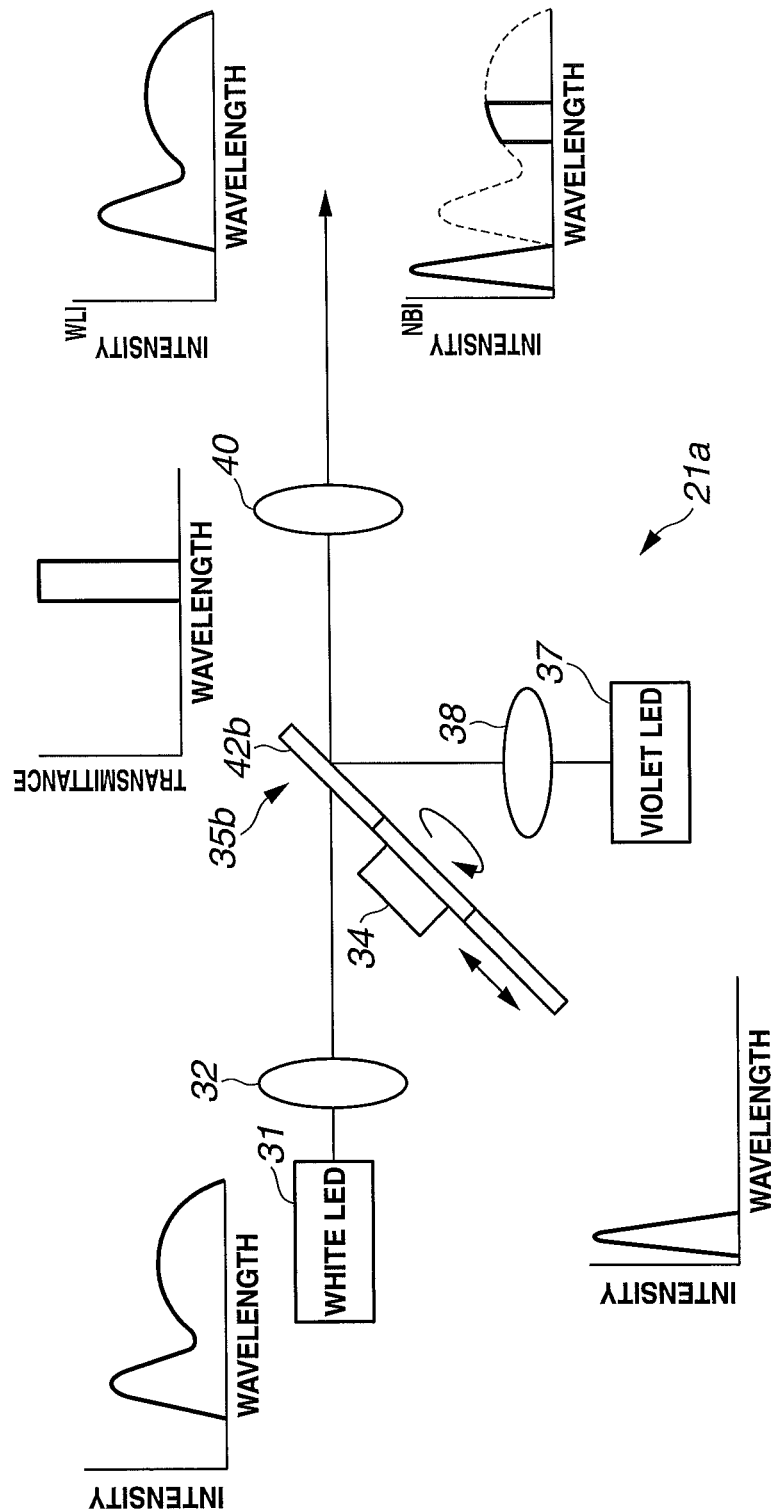

LIGHT SOURCE APPARATUS

CROSS REFERENCE TO RELATED APPLICATION

This application is a continuation application of PCT/JP2012/052723 filed on Feb. 7, 2012 and claims benefit of Japanese Application No. 2011-026370 filed in Japan on Feb. 9, 2011, the entire contents of which are incorporated herein by this reference.

BACKGROUND OF THE INVENTION

1. Field of the Invention

The present invention relates to a light source apparatus, and specifically relates to a light source apparatus enabling normal observation and special light observation to be performed simultaneously.

2. Description of the Related Art

Conventionally, light source apparatuses enabling special light observation such as narrow band observation (narrow band imaging: NBI) that enables observation of a site in the vicinity of a superficial portion of the mucous membrane of a living tissue in addition to normal observation (white light imaging: WLI) using white illumination have been developed (see, for example, Japanese Patent Laid-Open No. 2006-75239).

Such light source apparatuses include a turret including a plurality of optical filters, and mode switching between normal observation and special light observation is made by arranging an optical filter according to the observation mode in an optical path of a xenon lamp.

Furthermore, in recent years, with an increase in light amount of white LEDs, light source apparatuses using LEDs have been developed also in the field of endoscopes. Furthermore, in the field of endoscopes, there is a large demand for narrow band observation, and thus, light source apparatus configurations enabling narrow band observation using a white LED and a violet LED have been devised.

In such light source apparatuses, narrow band observation is performed by joining light from the violet LED to an optical path of the white LED using a dichroic filter that reflects a violet light band for narrow band observation. Then, the light source apparatuses are configured so as to insert/withdraw the dichroic filter to/from the optical path of the white LED according to the observation mode, whereby switching between normal observation and narrow band observation is made.

SUMMARY OF THE INVENTION

A light source apparatus according to an aspect of the present invention includes: a first light source that emits light including a first wavelength band and a second wavelength band; a second light source that emits light in a third wavelength band, the third wavelength band being different from the light in the first and second wavelength bands; an optical filter section including a transmission section that transmits light in the first wavelength band; an optical path joining section that reflects the light in the third wavelength band emitted from the second light source to join an optical path of the light in the third wavelength band to an optical path of the light emitted from the first light source; an illumination mode selection section for selecting at least one of first to third illumination modes; and an optical filter drive section that if the first illumination mode is selected in the illumination mode selection section, drives the optical filter section so that the transmission section is retracted from the optical path of the light emitted from the first light source, if the second illumination mode is selected, drives the optical filter section so that the transmission section is continuously inserted in the optical path of the light emitted from the first light source, and if the third illumination mode is selected, drives the optical filter section so that the transmission section is intermittently inserted in the optical path of the light emitted from the first light source.

BRIEF DESCRIPTION OF THE DRAWINGS

FIG. 4 is a diagram for describing an example where a position of a rotating disk is changed according to each of observation modes;

FIG. 5 is a diagram for describing an example of detection signals detected by a rotation detection section;

FIG. 6A is a diagram for describing an example of light adjustment control in a normal observation mode;

FIG. 6B is a diagram for describing an example of light adjustment control in a normal observation mode;

FIG. 7A is a diagram for describing an example of light adjustment control in a narrow band observation mode;

FIG. 7B is a diagram for describing an example of light adjustment control in a narrow band observation mode;

FIG. 8A is a diagram for describing an example of light adjustment control in a twin mode;

FIG. 8B is a diagram for describing an example of light adjustment control in a twin mode;

FIG. 12 is a diagram illustrating a configuration of an optical system according to a third embodiment;

FIG. 13A is a diagram for describing an example of light adjustment control in a normal observation mode in the third embodiment;

FIG. 13B is a diagram for describing an example of light adjustment control in a normal observation mode in the third embodiment;

FIG. 14A is a diagram for describing an example of light adjustment control in a twin mode in the third embodiment;

FIG. 15 is a diagram illustrating a configuration of an optical system according to a fourth embodiment.

DETAILED DESCRIPTION OF THE PREFERRED EMBODIMENTS

Embodiments of the present invention will be described in detail below with reference to the drawings.

First Embodiment

First, a configuration of an endoscope system including a light source apparatus according to a first embodiment of the present invention will be described with reference to FIG. 1.

Figure 1:
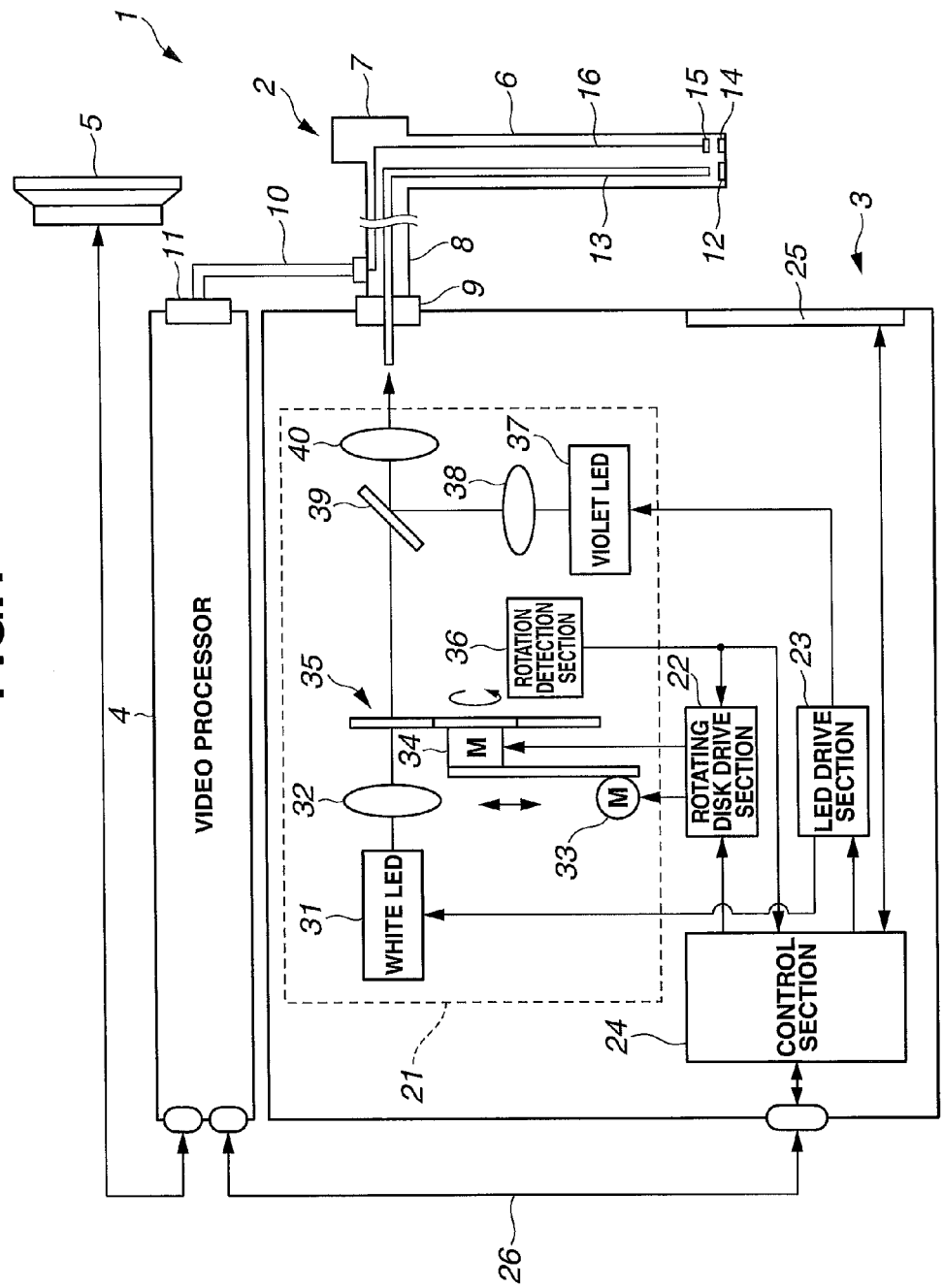
FIG. 1 is a diagram illustrating a configuration of an endoscope system including a light source apparatus according to a first embodiment of the present invention.

FIG. 1 is a diagram illustrating a configuration of an endoscope system including a light source apparatus according to a first embodiment of the present invention.

As illustrated in FIG. 1, an endoscope system 1 includes an endoscope 2 that picks up an image of an object inside a living body and outputs an image pickup signal, a light source apparatus 3 that supplies illuminating light for illuminating the object to the endoscope 2, a video processor 4 that converts the image pickup signal outputted from the endoscope 2 into a video signal and outputs the video signal, and a monitor 5 that displays an image according to the video signal outputted from the video processor 4.

The endoscope 2 includes an elongated insertion portion 6 that can be inserted into the inside of a living body, an operation portion 7 formed at a rear end of the insertion portion 6, a universal cable 8 extending out from the operation portion 7, a light source connector 9 provided at an end portion of the universal cable 8, an electric cable 10 extending out from a side portion of the light source connector 9, and an electric connector 11 provided at an end portion of the electric cable 10. The endoscope 2 is detachably attached to the light source apparatus 3 via the light source connector 9 provided at the end portion of the universal cable 8, and is detachably attached to the video processor 4 via the electric connector 11 provided at the end portion of the electric cable 10.

In a distal end portion of the insertion portion 6, an illumination lens 12 that illuminates an observation target is provided. On a rear end face of the illumination lens 12, a distal end portion of a light guide 13 that guides illuminating light is provided. The light guide 13 is inserted through the insertion portion 6, the operation portion 7 and the universal cable 8 and is connected to the light source apparatus 3 via the light source connector 9. With such configuration as described above, illuminating light emitted from the light source apparatus 3 is supplied to the illumination lens 12 via the light guide 13 and illuminates an object in front of the insertion portion 6.

Also, in the distal end portion of the insertion portion 6, an objective lens 14 that forms an optical image of an illuminated object is provided adjacent to the illumination lens 12. At a position where an image of an object is formed via the objective lens 14, an image pickup device 15 such as a CCD is provided. The image pickup device 15 subjects the formed optical image to photoelectric conversion to generate an image pickup signal. A signal wire 16 is connected to the image pickup device 15. The signal wire 16 is connected to the video processor 4 via the electric cable 10 and the electric connector 11. Consequently, the image pickup signal generated by the image pickup device 15 is supplied to the video processor 4 via the signal wire 16.

The video processor 4 subjects the image pickup signal supplied from the image pickup device 15 to signal processing by means of a non-illustrated video signal processing circuit to generate a video signal. The video processor 4 outputs the video signal to the monitor 5 to display the video signal on a display screen of the monitor 5.

Next, a configuration of the light source apparatus 3 will be described with reference to FIGS. 1 to 3.

Figure 2:
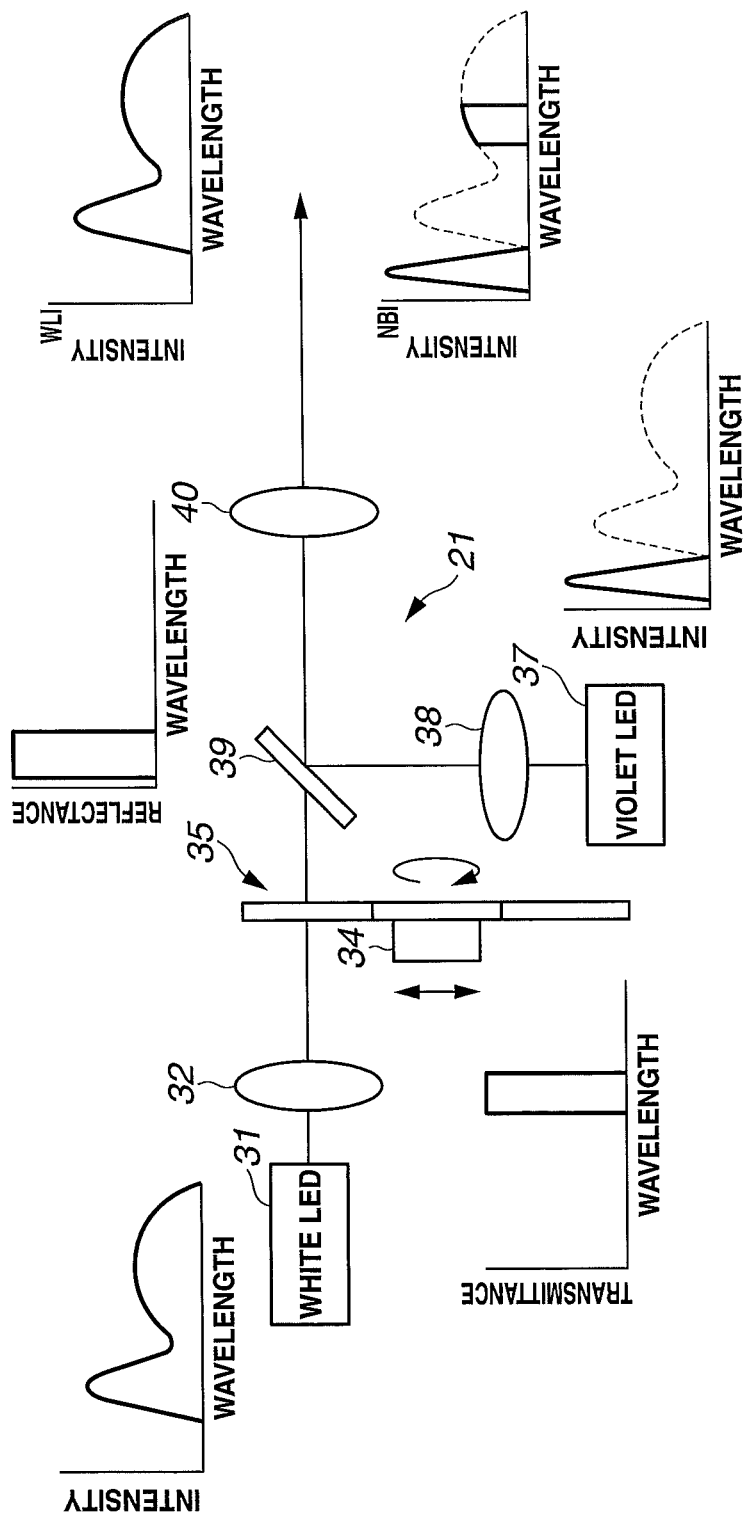
FIG. 2 is a diagram illustrating a detailed configuration of an optical system.
Figure 3:
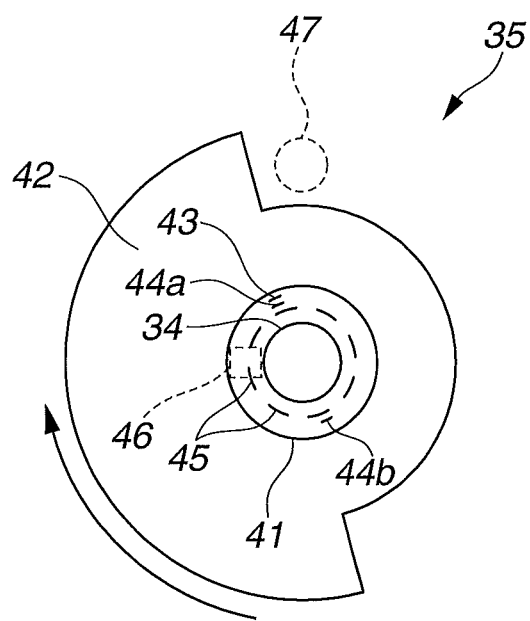
FIG. 3 is a diagram illustrating a detailed configuration of a rotating disk.

FIG. 2 is a diagram illustrating a detailed configuration of an optical system, and FIG. 3 is a diagram illustrating a detailed configuration of a rotating disk.

The light source apparatus 3 includes an optical system 21, a rotating disk drive section 22, an LED drive section 23, a control section 24, an operation panel 25 and a communication cable 26.

The optical system 21 includes a white LED 31, a lens 32, a movement motor 33, a rotation motor 34, a rotating disk 35, a rotation detection section 36, a violet LED 37, a lens 38, a dichroic filter 39 and a lens 40.

The white LED 31, which is a first light source, emits light including a first wavelength band around 540 nm, which is used for narrow band observation, and a second wavelength band of 430 to 700 nm with the first wavelength band (around 540 nm) excluded. The lens 32 is provided on an optical path of light emitted from the white LED 31, and collects the light emitted from the white LED 31.

The movement motor 33 vertically moves the rotating disk 35 relative to an optical path 47 of the white LED 31 (see FIG. 3) based on control performed by the rotating disk drive section 22, to insert/withdraw the rotating disk 35 to/from the optical path 47 of the white LED 31. The insertion/withdrawal of the rotating disk 35 is performed according to the observation mode. In the present embodiment, there are three observation modes, i.e., a normal observation mode, a narrow band observation mode and a twin mode in which an image according to normal observation and an image according to narrow band observation are simultaneously displayed.

When an observation mode is selected by a user operating the operation panel 25, which is an illumination mode selection section, an observation mode signal is supplied from the operation panel 25 to the control section 24. Note that the observation mode may be changed via, e.g., a non-illustrated operation switch provided at the operation portion 7 of the endoscope 2 or a non-illustrated operation switch provided at the video processor 4.

The control section 24 supplies a control signal according to the observation mode signal supplied from the operation panel 25 to the rotating disk drive section 22. Upon receipt of the control signal from the control section 24, the rotating disk drive section 22 controls the movement motor 33 to vertically move the rotating disk 35 relative to the optical path 47 of the white LED 31 to a position according to the selected observation mode.

The rotation motor 34 rotates the rotating disk 35 at a fixed speed of 30 Hz (one frame) based on control performed by the rotating disk drive section 22. The rotating disk drive section 22 controls the rotation motor 34 according to a rotation speed of the rotating disk 35 supplied from the later-described rotation detection section 36.

As illustrated in FIG. 3, the rotating disk 35, which is an optical filter section, includes the rotation motor 34, a disk body 41 and a filter 42 having a shape formed by combining two semicircles having different diameters.

When the filter 42, which is a transmission section, is inserted in the optical path 47 of the white LED 31, the filter 42 transmits light in a first wavelength band around 540 nm, which is used for narrow band observation, from light including the first and second wavelength bands from the white LED 31.

At the disk body 41, a rotation detection silk 43 for detecting rotation, two filter position detection silks 44a and 44b for detecting a position of the filter 42, in particular, the two semicircles having different diameters, and a plurality of, eight in FIG. 3, rotation speed detection silks 45 for detecting a rotation speed of the rotating disk 35, the rotation speed detection silks 45 being provided at predetermined intervals. Note that the count of rotation speed detection silks 45 is not limited to eight and may be another count.

Note that at the disk body 41, a silk detection position 46 for detecting the rotation detection silk 43, the filter position detection silks 44a and 44b and the rotation speed detection silk 45 is provided.

The rotation detection section 36 is, for example, a photo-reflector, which emits light to the silk detection position 46 and receives reflected light, thereby detecting a rotation speed and a rotational position of the rotating disk 35. Then, the rotation detection section 36 sends a rotation speed signal indicating the detected rotation speed to the rotating disk drive section 22 and sends a rotational position signal indicating the rotational position to the control section 24.

The rotating disk drive section 22 performs speed servo control based on the rotation speed signal from the rotation detection section 36 to control the rotating disk 35 to rotate at a fixed speed of 30 Hz (one frame).

The control section 24 sends the rotational position signal to the video processor 4 via the communication cable 26 to enable synchronization of LED illumination and image processing. Also, the control section 24 receives a brightness signal from the video processor 4 and calculates a light adjustment value (LED current value or LED light-up duty ratio) to provide proper brightness of the screen of the monitor 5. The control section 24 outputs light-up current signals and light-up/off signals for the white LED 31 and the violet LED 37 to the LED drive section 23, based on the observation mode, the rotational position and the light adjustment information.

The LED drive section 23 performs driving of the white LED 31 and the violet LED 37 according to the light-up current signals and the light-up/off signals supplied from the control section 24.

The violet LED 37, which is a second light source, emits light in a third wavelength band around 415 nm, which is different from the first and second wavelength bands. The lens 38 is provided on an optical path of light emitted by the violet LED 37, and collects the light emitted from the violet LED 37.

The dichroic filter 39, which is an optical path joining section, reflects light having wavelengths around 415 nm (third wavelength band) from the violet LED 37, and transmits light in a wavelength band other than the third wavelength band. The dichroic filter 39 reflects light emitted from the violet LED 37 and collected by the lens 38 so as to join the optical path of the violet LED 37 to the optical path 47 of light emitted from the white LED 31.

The lens 40 collects light from the dichroic filter 39 and supplies the light to an incident end face of the light guide 13, which projects from the light source connector 9.

Next, an operation of the light source apparatus 3 will be described.

When an operator selects an observation mode via the operation panel 25, an observation mode signal is supplied from the operation panel 25 to the control section 24. The control section 24 supplies a control signal according to the observation mode signal to the rotating disk drive section 22. The rotating disk drive section 22 controls the movement motor 33 according to the control signal from the control section 24.

FIG. 4 is a diagram for describing an example where a position of the rotating disk is changed according to each of the observation modes.

If the normal observation mode, which is a first illumination mode, is selected, the rotating disk drive section 22, which is an optical filter drive section, drives the movement motor 33 to change the position of the rotating disk 35 so that the filter 42 is retracted from the optical path 47 of light emitted from the white LED 31 as illustrated in a position A in FIG. 4. Consequently, the filter 42 is consistently not inserted in the optical path 47 of the white LED 31.

The LED drive section 23 drives the white LED 31 to be lit up and the violet LED 37 to be lit off in a state in which the filter 42 is not inserted in the optical path 47 of the white LED 31. Consequently, light for normal observation, which includes the first and second wavelength bands, from the white LED 31 is consistently emitted from the light source apparatus 3, enabling normal observation using the white LED 31.

Furthermore, if the narrow band observation mode, which is a second illumination mode, is selected, the rotating disk drive section 22 drives the movement motor 33 to change the position of the rotating disk 35 so that the filter 42 is continuously inserted in the optical path 47 of light emitted from the white LED 31 as illustrated in a position B in FIG. 4. Consequently, the filter 42 is consistently inserted in the optical path 47 of the white LED 31.

The LED drive section 23 drives the white LED 31 and the violet LED 37 to enter a lit-up state when the filter 42 is consistently inserted in the optical path 47 of the white LED 31. Consequently, light for narrow band observation, which is obtained by combining light in the first wavelength band emitted by the white LED 31 and passed through the filter 42 and light in the third wavelength band emitted from the violet LED 37 and reflected by the dichroic filter, is consistently emitted from the light source apparatus 3, enabling narrow band observation using the white LED 31 and the violet LED 37.

Also, if the twin mode, which is a third illumination mode, is selected, the rotating disk drive section 22 drives the movement motor 33 to change the position of the rotating disk 35 so that the filter 42 is intermittently inserted in the optical path 47 of the light emitted from the white LED 31 as illustrated in a position C in FIG. 4. Consequently, the filter 42 is intermittently inserted in the optical path 47 of the white LED 31. In other words, the filter 42 is inserted/withdrawn to/from the optical path 47 of the white LED 31 every half turn (every 60 Hz) of the rotating disk 35.

The LED drive section 23 drives the white LED 31 to be consistently lit up in such state, whereby light for normal observation, which includes the first and second wavelength bands, and light in the first wavelength band passed through the filter 42 for narrow band observation are alternately outputted to the dichroic filter 39 at a cycle of one field (60 Hz).

FIG. 5 is a diagram for describing an example of detection signals detected by the rotation detection section.

The rotation detection section 36 generates a rotation detection signal from the rotation detection silk 43, generates a filter position detection signal from the filter position detection silks 44a and 44b, and generates a rotation speed detection signal from the rotation speed detection silk 45. In particular, the rotation detection section 36 detects a rotational position of the rotating disk 35 from the rotation detection signal and the filter position detection signal to detect a timing for inserting/withdrawing the filter 42 to/from the optical path 47 of the white LED 31.

The LED drive section 23 drives the violet LED 37 so as to be lit up during a period in which the filter 42 is inserted in the optical path 47 of the white LED 31, and lit off during a period in which the filter 42 is not inserted in the optical path 47 of the white LED 31. Consequently, light in the third wavelength band is outputted to the dichroic filter 39 at a timing that is the same as a timing for outputting light in the first wavelength band passed through the filter 42 for narrow band observation to the dichroic filter 39. At a timing for outputting light for normal observation, which includes the first and second wavelength bands, to the dichroic filter 39, the violet LED 37 is lit off, and thus, light for normal observation is outputted to the dichroic filter 39. According to the above, the light source apparatus 3 according to the present embodiment enables white light for normal observation and narrow band observation light for narrow band observation to be alternately emitted at a cycle of one field (60 Hz).

The control section 24 in the light source apparatus 3 sends a rotational position signal indicating a timing for inserting/withdrawing the filter 42 to/from the optical path 47 of the white LED 31 to the video processor 4 as a synchronizing signal. Using the synchronizing signal, the video processor 4 alternately performs observation processing for normal observation and narrow band observation every one field (60 Hz) and outputs images resulting from the image processing to the monitor 5. Consequently, the monitor 5 can simultaneously display an image according to normal observation and an image according to narrow band observation.

Next, light adjustment control in each of the observation modes will be described with reference to FIGS. 6 to 9.

It is desirable that light adjustment control be performed by means of PWM control because LEDs create color changes (wavelength shifts) according to the current values. Setting of a current value for each of the observation modes is made taking, e.g., color balance into account at, e.g., the factories.

FIGS. 6A and 6B are diagrams for describing an example of light adjustment control in the normal observation mode.

FIG. 6A indicates a state of current control for a maximum light amount value for the normal observation mode, and at a current value $I_1$, the white LED 31 is on and the violet LED 37 is off.

The control section 24 communicates with the video processor 4 via the communication cable 26 and receives a brightness control signal. The control section 24 receives the brightness control signal, and if the light amount is controlled to 50%, sends a control signal for controlling the light amount to 50% to the LED drive section 23. Based on the control signal, the LED drive section 23 outputs a drive signal for making the white LED 31 have a duty ratio of 50% to the white LED 31 as illustrated in FIG. 6B.

FIGS. 7A and 7B are diagrams for an example of light adjustment control in the narrow band observation mode.

FIG. 7A indicates a state of current control for maximum light amount values for the narrow band observation mode, and the white LED 31 is on at a current value $I_2$ and the violet LED 37 is on at a current value $I_3$. If the light amount is controlled to 50%, the LED drive section 23 outputs drive signals for making the white LED 31 and the violet LED 37 have a duty ratio of 50% to the white LED 31 and the violet LED 37, respectively, based on the control signal from the control section 24 as illustrated in FIG. 7B.

As described above, in the narrow band observation mode, the current value $I_2$ for the white LED 31 and the current value $I_3$ for the violet LED 37 are set so that a substantial predetermined light amount ratio is provided between the amount of light in the first wavelength band emitted from the white LED 31 and passed through the filter 42 and the amount of light in the third wavelength band emitted from the violet LED 37.

FIGS. 8A and 8B are diagrams for describing an example of light adjustment control in the twin mode.

FIG. 8A indicates a state of current control for maximum light amount values in the twin mode, and the white LED 31 is on at a current value $I_4$ in narrow band observation, and the white LED 31 is on at a current value $I_6$ in normal observation. For normal observation in the twin mode, there is no need for the white LED 31 to take a ratio in light amount between the white LED 31 and the violet LED 37 into account, and thus, in narrow band observation, the white LED 31 can be on at the current value $I_6$, which is larger than the current value $I_4$. Furthermore, the violet LED 37 is on at a current value $I_5$ in narrow band observation and is off in normal observation.

If the light amount is controlled to 50%, the LED drive section 23 outputs drive signals for making the white LED 31 and the violet LED 37 have a duty ratio of 50% to the white LED 31 and the violet LED 37, respectively, based on a control signal from the control section 24 as illustrated in FIG. 8B.

Since in the twin mode, normal observation and narrow band observation are alternately performed, the violet LED 37 is lit up not consistently but in pulses at a half cycle of a rotation cycle of the rotating disk 35. Thus, the current value $I_4$ for the white LED 31 and the current value $I_5$ for the violet LED 37 in the twin mode can be made to be larger than the current value $I_2$ for the white LED 31 and the current value $I_3$ for the violet LED 37 in the narrow band observation mode. Furthermore, in narrow band observation in the twin mode, the current value $I_4$ for the white LED 31 and the current value $I_5$ for the violet LED 37 are set so that a substantial predetermined light amount ratio is provided between the amount of light in the first wavelength band emitted from the white LED 31 and passed through the filter 42 and the amount of light in the third wavelength band emitted from the violet LED 37.

As described above, if the narrow band observation mode or the twin mode is selected, the LED drive section 23, which is a light amount control section, controls the white LED 31 and the violet LED 37 so that a substantial predetermined light amount ratio is provided between the amount of light emitted from the white LED 31 and the amount of light emitted from the violet LED 37.

Furthermore, where the twin mode is selected, the LED drive section 23 changes the amount of light emitted from the white LED 31 to be different between in a narrow band observation period in which the violet LED 37 is lit up and in a normal observation period in which the violet LED 37 is not lit up.

Figure 9:
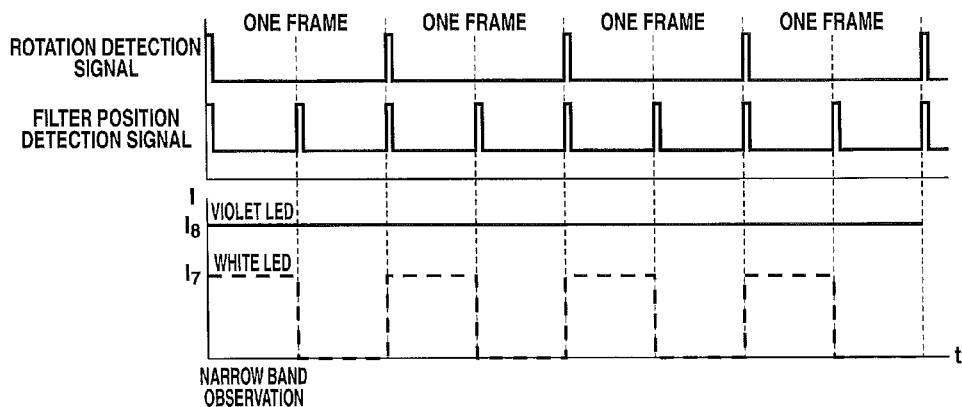
FIG. 9 is a diagram for describing another example of light adjustment control.
Figure 10:
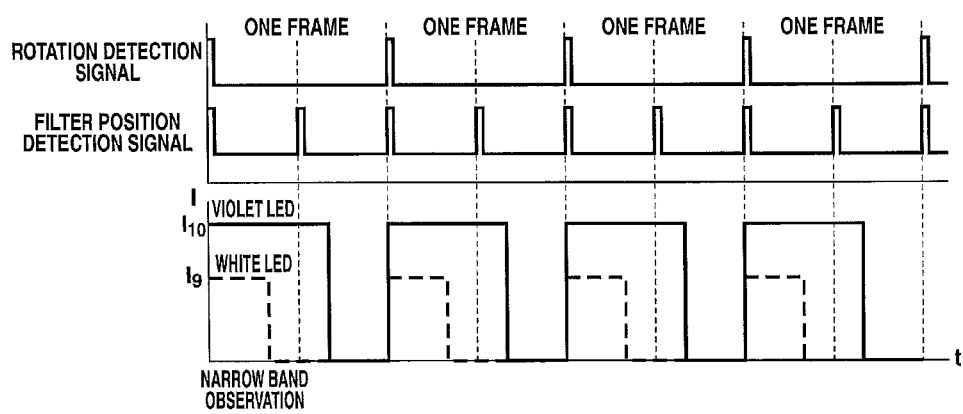
FIG. 10 is a diagram for describing still another example of light adjustment control.

FIGS. 9 and 10 are diagrams for describing other control examples of light adjustment control.

Although in FIG. 7A, only the current values are employed for making settings for providing a substantial predetermined light amount ratio between the amount of light in the first wavelength band and the amount of light in the third wavelength band emitted from the violet LED 37, the settings can be made using both the current values and the duty ratios. In FIG. 9, a substantial predetermined light amount ratio is provided by a combination of a current value $I_8$ and a duty ratio of 100% for the violet LED 37 and a current value $I_7$ and a duty ratio of 50% for the white LED 31. Furthermore, in FIG. 10, a substantial predetermined light amount ratio is provided by a combination of a current value $I_{10}$ and a duty ratio of 70% for the violet LED 37 and a current value $I_9$ and a duty ratio of 30% for the white LED 31.

Note that in light adjustment, duty ratio adjustment is made so that the substantial predetermined light amount ratio is not changed. If the amount of light is changed to 50% from the state in FIG. 9, it is only necessary to make the violet LED 37 have a duty ratio of 50% and the white LED 31 have a duty ratio of 25%. Furthermore, if the light amount is changed to 50% from the state in FIG. 10, it is only necessary to make the violet LED 37 have a duty ratio of 35% and the white LED 31 have a duty ratio of 15%.

As described above, the light source apparatus 3 is configured so that light for normal observation, which is emitted from the white LED 31, and light for narrow band observation, which is obtained from combining light emitted from the violet LED 37 with light emitted from the white LED 31 and subjected to band limitation by the filter 42, are alternately emitted at a cycle of one field (60 Hz). The video processor 4 performs image processing for normal observation and narrow band observation are alternately performed every one field (60 Hz), and outputs images resulting from the image processing to the monitor 5, whereby an image according to normal observation and an image according to narrow band observation are simultaneously displayed on the monitor 5.

Accordingly, the light source apparatus 3 according to the present embodiment enables an image according to normal observation and an image according to special light observation to be simultaneously displayed on the monitor.

Second Embodiment

Next, a second embodiment will be described.

A configuration of a light source apparatus according to the second embodiment uses a rotating disk 35a instead of the rotating disk 35 in the first embodiment.

Figure 11:
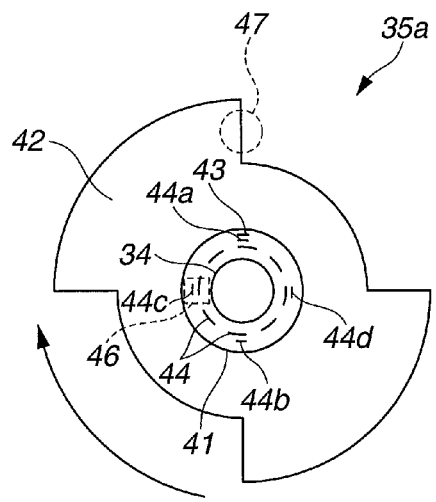
FIG. 11 is a diagram illustrating a configuration of a rotating disk according to a second embodiment.

FIG. 11 is a diagram illustrating a configuration of a rotating disk according to the second embodiment.

As illustrated in FIG. 11, the rotating disk 35a includes a filter 42a. Although the filter 42 in the first embodiment has a shape formed by combining two semicircles having different diameters, the filter 42a in the present embodiment has a shape formed by alternately combining two quarter circles having different diameters. Furthermore, filter position detection silks 44c and 44d for detecting a rotational position of such filter 42a are added to a disk body 41.

A rotation motor 34 rotates the rotating disk 35a at a fixed speed of 15 Hz, which is half of that of the first embodiment, based on control performed by the rotating disk drive section 22.

With a light source apparatus 3 according to the present embodiment as described above, in a twin mode, the filter 42 is inserted/withdrawn to/from an optical path 47 of a white LED 31 every one field (60 Hz). As a result, the light source apparatus 3 according to the present embodiment enables normal observation and narrow band observation to be performed every one field (60 Hz) as in the first embodiment.

Furthermore, in the light source apparatus 3 according to the present embodiment, the rotating disk 35a includes the filter 42a having a shape formed by alternately combining two quarter circles having different diameters, and thus, a gravity center of the rotating disk 35a and a center of rotation can be made to be correspond to each other. As a result, the light source apparatus 3 according to the present embodiment enables enhancement in stability of rotation of the rotating disk 35a compared to the rotating disk 35 in the first embodiment.

Third Embodiment

Next, a third embodiment will be described.

A configuration of a light source apparatus according to the third embodiment is substantially similar to that of the first embodiment, and thus, a description will be provided only in terms of differences.

FIG. 12 is a diagram illustrating a configuration of an optical system according to the third embodiment. Note that the rotating disk 35a according to the second embodiment may be employed instead of a rotating disk 35.

In the present embodiment, in addition to narrow band observation, in normal observation, in particular, in normal observation in a normal observation mode and normal observation in a twin mode, also, a violet LED 37 is lit up. An LED drive section 23 outputs a drive signal for lighting up the violet LED 37 in normal observation to the violet LED 37, based on control performed by the control section 24. However, an intensity of the violet LED 37 in normal observation is lower than that in narrow band observation.

In normal observation, a dichroic filter 39 reflects light including a third wavelength band emitted from the violet LED 37 to combine the light with light including first and second wavelength bands emitted from the white LED 31.

Light including the first to third wavelength bands resulting from the combination via the dichroic filter 39 is collected by the lens 40 and supplied to an incident end face of a light guide 13, which projects from a light source connector 9. The rest of configuration is similar to that of the first embodiment.

Next, light adjustment control in each of the observation modes will be described with reference to FIGS. 13 and 14.

FIGS. 13A and 13B are diagrams for an example of light adjustment control in the normal observation mode in the third embodiment.

FIG. 13A indicates a state of current control for maximum light amount values in the normal observation mode. Although in the normal observation mode according to the first embodiment, the violet LED 37 is off as illustrated in FIG. 6A, in the normal observation mode according to the present embodiment, the violet LED 37 is on at a current value $I_{11}$ as illustrated in FIG. 13A.

If the light amount is controlled to 50%, an LED drive section 23 outputs drive signals for making the white LED 31 and the violet LED 37 have a duty ratio of 50% to the white LED 31 and the violet LED 37, respectively, based on a control signal from the control section 24 as illustrated in FIG. 13B.

Note that light adjustment control in narrow band observation is similar to that in FIGS. 7A and 7B in the first embodiment, and a description thereof will be omitted.

Figure 14B:
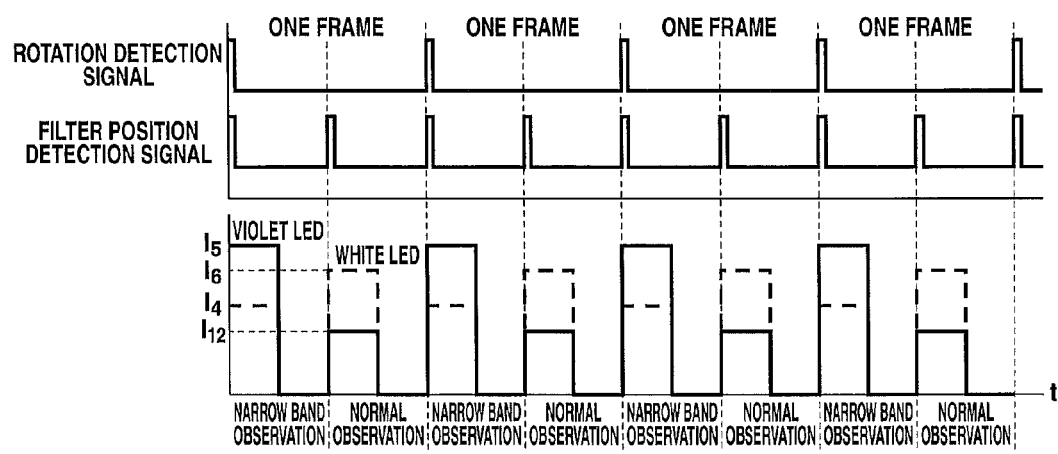
FIG. 14B is a diagram for describing an example of light adjustment control in a twin mode in the third embodiment.

FIGS. 14A and 14B are diagrams for describing an example of light adjustment control in the twin mode according to the third embodiment.

FIG. 14A indicates a state of current control for a maximum light amount value in the twin mode. Although in normal observation in the twin mode in the first embodiment, the violet LED 37 is off as illustrated in FIG. 8A, in normal observation in the twin mode in the present embodiment, the violet LED 37 is on at a current value $I_{12}$ as illustrated in FIG. 14A.

If the light amount is controlled to 50%, the LED drive section 23 outputs drive signals for making the white LED 31 and the violet LED 37 have a duty ratio of 50% to the white LED 31 and the violet LED 37, respectively, based on a control signal from the control section 24 as illustrated in FIG. 14B.

The light source apparatus 3 according to the present embodiment described above enables easy observation of blood vessels in a superficial portion of a mucous membrane in normal observation.

Fourth Embodiment

Next, a fourth embodiment will be described.

A configuration of a light source apparatus according to the fourth embodiment uses an optical system 21a instead of the optical system 21 in the first embodiment.

FIG. 15 is a diagram illustrating a configuration of an optical system according to the fourth embodiment.

The optical system 21a includes a rotating disk 35b arranged obliquely relative to an optical path 47 of a white LED 31. The rotating disk 35b is obliquely inserted/withdrawn to/from the optical path 47 of the white LED 31 via a movement motor 33.

Also, the rotating disk 35b includes a filter 42b with a filter that transmits white light to green light from the white LED 31 and a filter that reflects violet light from a violet LED 37 integrated therein. In other words, the filter 42b is a filter with the filter 42 and the dichroic filter 39 in the first embodiment integrated therein.

With the light source apparatus 3 according to the present embodiment described above, if an accuracy in position of the rotating disk 35b is low, which results in a substantial decrease in amount of violet light emitted, it is necessary to enhance the accuracy in position of the rotating disk 35b; however, the light source apparatus 3 according to the present embodiment enables cost reduction and downsizing due to reduction in number of parts compared to the light source apparatus 3 according to the first embodiment.

The present invention is not limited to the above-described embodiments, and various modifications, alterations and the like are possible without departing from the spirit of the present invention.

What is claimed is:

1. A light source apparatus comprising:
    a first light source that emits light including a first wavelength band and a second wavelength band;
    a second light source that emits light in a third wavelength band, the third wavelength band being different from the light in the first and second wavelength bands;
    an optical filter section including a transmission section that transmits light in the first wavelength band;
    an optical path joining section that reflects the light in the third wavelength band emitted from the second light source to join an optical path of the light in the third wavelength band to an optical path of the light emitted from the first light source;
    an illumination mode selection section for selecting at least one of first to third illumination modes; and
    an optical filter drive section that if the first illumination mode is selected in the illumination mode selection section, drives the optical filter section so that the transmission section is retracted from the optical path of the light emitted from the first light source, if the second illumination mode is selected, drives the optical filter section so that the transmission section is continuously inserted in the optical path of the light emitted from the first light source, and if the third illumination mode is selected, drives the optical filter section so that the transmission section is intermittently inserted in the optical path of the light emitted from the first light source.

2. The light source apparatus according to claim 1, wherein if the first illumination mode is selected in the illumination mode selection section, the second light source is lit up to make light from the second light source enter the optical path of the light emitted from the first light source.

3. The light source apparatus according to claim 1, further comprising a light amount control section that if the second illumination mode or the third illumination mode is selected in the illumination mode selection section, controls a light amount of at least any one of an amount of the light from the first light source and an amount of the light from the second light source so that a substantial predetermined light amount ratio is provided between an amount of light in the second wavelength band emitted from the first light source and passed through the transmission section and an amount of the light in the third wavelength band emitted from the second light source.

4. The light source apparatus according to claim 3, wherein if the third illumination mode is selected in the illumination mode selection section, the light amount control section changes the amount of the light emitted from the first light source to be different between in a period in which the second light source is lit up and in a period in which the second light source is not lit up.

5. The light source apparatus according to claim 1, wherein the optical filter section has a shape formed by combining two semicircles having different diameters.

6. The light source apparatus according to claim 5, wherein if the third illumination mode is selected in the illumination mode selection section, the optical filter drive section drives the optical filter to rotate at a position where a part of the two semicircles, the part having a large diameter, is inserted in an optical path of the illuminating light and a part of the two semicircles, the part having a small diameter, is not inserted in the optical path of the illuminating light.

7. The light source apparatus according to claim 1, wherein the optical filter section has a shape formed by alternately combining two quarter circles having different diameters.

8. The light source apparatus according to claim 7, wherein if the third illumination mode is selected in the illumination mode selection section, the optical filter drive section drives the optical filter to rotate at a position where parts of the quarter circles, the parts having a large diameter, are inserted in the optical path of the illuminating light and parts of the quarter circles, the parts having a small diameter, are not inserted in the optical path of the illuminating light.

* * * * *